United States Patent [19]

Robins et al.

[11] Patent Number: 5,273,903
[45] Date of Patent: Dec. 28, 1993

[54] BIOTECHNOLOGICAL PROCESS FOR THE PRODUCTION OF S-(+)-2,2-DIMETHYLCYCLOPROPANECARBOXAMIDE

[75] Inventors: Karen Robins, Visp; Thomas Gilligan, Leuk, both of Switzerland

[73] Assignee: Lonza Ltd., Gampel/Valais, Switzerland

[21] Appl. No.: 845,034

[22] Filed: Mar. 3, 1992

[30] Foreign Application Priority Data

Mar. 6, 1991 [CH] Switzerland ............... 0678/91
Jun. 24, 1991 [CH] Switzerland ............... 01854/91

[51] Int. Cl.$^5$ ..................... C12P 41/00; C12P 7/40
[52] U.S. Cl. ..................... 435/280; 435/136; 435/822; 435/874
[58] Field of Search ............ 435/280, 136, 129, 822, 435/874

[56] References Cited

U.S. PATENT DOCUMENTS

2,511,867  6/1950  Neuberg ................ 195/29

FOREIGN PATENT DOCUMENTS

| | | |
|---|---|---|
| 251111 | 4/1988 | Czechoslovakia . |
| 0048301 | 3/1982 | European Pat. Off. . |
| 0155779 | 9/1984 | European Pat. Off. . |
| 0264457 | 4/1988 | European Pat. Off. . |

OTHER PUBLICATIONS

"The Prokaryotes" edited by Balows et al., p. I-16, 1992.
Kulla et al., Arch. Microbiol., 135, (1983), pp. 1 to 7.

*Primary Examiner*—Douglas W. Robinson
*Assistant Examiner*—S. Saucier
*Attorney, Agent, or Firm*—Fisher, Christen & Sabol

[57] ABSTRACT

A microbiological process for the production of S-(+)-2,2-dimethylcyclopropanecarboxamide, starting from R,S-(±)-2,2-dimethylcyclopropanecarboxamide. For this process, new microorganisms are selected and isolated, which are capable of biotransforming R-(−)-2,2-dimethylcyclopropanecarboxamide in racemic 2,2-dimethylcyclopropanecarboxamide to R-(−)-2,2-dimethylcyclopropanecarboxylic acid. The process can then be performed either with the microorganisms or with the cell-free enzymes from the microorganisms.

22 Claims, No Drawings

BIOTECHNOLOGICAL PROCESS FOR THE PRODUCTION OF S-(+)-2,2-DIMETHYLCYCLOPROPANECARBOXAMIDE

BACKGROUND OF THE INVENTION

1. Field of the Invention

The invention relates to a new process for the production of optically active S-(+)-2,2-dimethylcyclopropanecarboxamide, in which the R-(−)-2,2-dimethylcyclopropanecarboxamide in racemic R,S-(±)-2,2-dimethylcyclopropanecarboxamide is biotransformed to R-(−)-2,2-dimethylcyclopropanecarboxylic acid and in this way the desired S-(+)-2,2-dimethylcyclopropanecarboxamide is obtained.

Below, 2,2-dimethylcyclopropanecarboxamide may be abbreviated 2,2-DMCPCA and 2,2-dimethylcyclopropanecarboxylic acid may be abbreviated 2,2-DMCPCS.

2. Background Art

Optically pure S-(+)-2,2-DMCPCA is used as the initial material for the production of the dehydropeptidase inhibitor cilastatin, which is administered in treatment together with penem or carbapenem antibiotics, to prevent the deactivation of the antibiotics by a renal dehydropeptidase in the kidneys [European Published Patent Application No. 048301].

Previously, only chemical processes for the production of S-(+)-2,2-DMCPCA were known. These processes have the drawback that they are expensive and take place by several stages [European Published Patent Application No. 155779].

BROAD DESCRIPTION OF THE INVENTION

The main object of the invention is to provide a biotechnological process with which the desired isomer can be obtained in high purity in a step starting from easily obtainable racemic R,S-(±)-2,2-DMCPCA Other objects and advantages of the invention are set out herein or are obvious to one skilled in the art.

The objects and advantages of the invention are achieved by the process and microorganisms of the invention.

The invention involves a process for the production of S-(+)-2,2-dimethylcyclopropanecarboxamide. R-(−)-2,2-dimethylcyclopropanecarboxamide in racemic R,S-(±)-2,2-dimethylcyclopropanecarboxamide is biotransformed to R-(−)-2,2-dimethylcyclopropanecarboxylic acid, and optically active S-(+)-2,2-dimethylcyclopropanecarboxamide is obtained. The latter is isolated.

Preferably the biotransformation is performed with a microorganism. Also preferably the biotransformation is performed with an enzyme from a microorganism in a cell-free system. Preferably the biotransformation is performed in a medium containing racemic 2,2-dimethylcyclopropanecarboxamide in an amount of 0.2 to 5 percent by weight. Preferably the biotransformation is performed at a pH of 6 to 11 and at a temperature of 15° to 55° C.

Preferably the biotransformation is performed with microorganisms of the species Comamonas acidovorans A:18 (DSM No. 6315) or descendants thereof or mutants thereof. Preferably the biotransformation is performed either with microorganism of the species Comamonas acidovorans TG 308 (DSM No. 6552) or descendants or mutants thereof, or with cell-free enzymes from these microorganisms. Preferably the biotransformation is performed either with microorganisms of the species Pseudomonas sp. NSAK:42 (DSM No. 6433) or descendants or mutants thereof, or with cell-free enzymes from these microorganisms. Preferably the biotransformation is performed either with microorganisms of the species Bacterium sp. VIII:II (DSM No. 6316) or descendants or mutants thereof, or with cell-free enzymes from these microorganisms.

The invention also involves (biologically pure cultures of) microorganisms, which are capable of biotransforming R-(−)-2,2-dimethylcyclopropanecarboxamide in racemic R,S-(±)-2,2-dimethylcyclopropanecarboxamide to R-(−)-2,2-dimethylcyclopropanecarboxylic acid, with optically active S-(+)-2,2-dimethylcyclopropanecarboxamide being obtained.

Preferably the microorganisms are obtained according to the following selection methods:

(a) microorganisms, which are cultivated with 2,2-dimethylcyclopropanecarboxamide in the form of the racemate or its optical isomers as an N-source and grow with a C-source; and (b) from the culture obtained by cultivation, those are then selected which are stable and use 2,2-dimethylcyclopropanecarboxamide in the form of the racemate or its optical isomers as the sole N-source.

Preferably the microorganisms are those which, as a C-source, use sugars, sugar alcohols, carboxylic acids, alcohols or other C-sources as a growth substrate. Preferably biologically pure cultures of the microorganisms are those which accept R-(−)-2,2-dimethylcyclopropanecarboxamide as an N-source.

The microorganisms preferably are: biologically pure cultures of the microorganism Comamonas acidovorans A:18 (DSM No. 6315), or descendants or mutants thereof; (biologically pure cultures of) the microorganism Comamonas acidovorans TG 308 (DSM No. 6552), or descendants or mutants thereof; (biologically pure cultures of) the microorganism Pseudomonas sp. NSAK:42 (DSM No. 6433), or descendants or mutants thereof; and (biologically pure cultures of) the microorganism Bacterium sp. VIII:II (DSM No. 6316), or descendants or mutants thereof.

DETAILED DESCRIPTION OF THE INVENTION

The microorganisms according to the invention are capable of biotransforming R-(−)-2,2-DMCPCA in racemic R,S-(±)-2,2-DMCPCA to R-(−)-2,2-DMCPCS, and optically active S-(+)-2,2-DMCPCA is obtained. The microorganisms can be isolated, for example, from soil samples, sludge or waste water with the help of traditional microbiological techniques. According to the invention, all microorganisms which use R-(−)-DMCPCA as a substrate are suitable for the production of S-(+)-2,2-DMCPCA.

The microorganisms of the invention are obtainable according to the following method of selection:

(a) microorganisms, which grow with 2,2-DMCPCA, in the form of the racemate or its optical isomers, as an N-source and with a C-source, are cultivated in the usual (known) way; and (b) from the culture obtained by cultivation, those are then selected which are stable and use 2,2-DMCPCA in the form of a racemate or its optical isomers as the sole N-source. Suitably, the microorganisms are selected which accept R-(−)-2,2-DMCPCA as an N-source.

As a C-source, the microorganisms can use, for example, sugars, sugar alcohols, carboxylic acids or alcohols as growth substrates. As sugar, for example, fructose or glucose can be used. As sugar alcohols, for example, erythritol, mannitol or sorbitol can be used. As carboxylic acids, mono-, di- or tricarboxylic acids, such as, acetic acid, malonic acid or citric acid, can be used. As alcohols, monovalent, divalent or trivalent alcohols, such as, ethanol, glycol or glycerin, can be used. Preferably, a trivalent alcohol, such as, for example, glycerin, is used as the C-source.

Suitably, the C/N ratio in the selection medium is in a range between 5:1 and 10:1.

As a selection medium, the media usual among experts can be used, such as, a mineral salt medium, described in Kulla et al., Arch. Microbiol., 135, (1983), pages 1 to 7.

Preferred microorganisms, which grow with 2,2-DMCPCA, in the form of the racemate or one of its optical isomers, as an N-source and with a C-source, are: *Comamonas acidovorans* A:18 (DSM No. 6315); *Comamonas acidovorans* TG 308 (DSM No. 6552); Pseudomonas sp. NSAK:42 (DSM No. 6433); and microorganism Bacterium sp. VIII:II (DSM No. 6316); as well as their descendants and mutants.

The strains of DSM No. 6315 and 6316 were deposited on Jan. 29, 1991, those of DSM No. 6433 on Mar. 25, 1991, and those of DSM No. 6552 on Apr. 6, 1991, with the Deutsche Sammlung von Mikroorganismen und Zellkulturen GmbH (German Collection of Microorganisms and Cell Cultures GmbH), Mascherodeweg 1B, D-3300 Brunswick, Germany.

The scientific (taxonomic) description of *Comamonas acidovorans* A:18 (DSM No. 6315), is:

| | |
|---|---|
| cell shape | rods |
| width micron | 0.5 to 0.7 |
| length micron | 1.5 to 3.0 |
| mobility | + |
| flagella | polar > 1 |
| Gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.6 | + |
| MacConkey agar | + |
| SS agar | + |
| cetrimide agar | + |
| pigments | |
| nondiffusing | − |
| diffusing | − |
| fluorescent | − |
| pyocyanin | − |
| acid from (OF test) | |
| glucose, aerobic | − |
| glucose, anaerobic | − |
| gas from glucose | − |
| acid from | |
| glucose | − |
| fructose | + |
| xylose | − |
| mannitol | + |
| glycerol | + |
| ONPG | − |
| ADH | − |
| VP | − |
| indole | − |
| NO$_2$ from NO$_3$ | + |
| denitrification | − |
| phenylalaninedesaminase | − |
| levan from saccharose | − |
| lecithinase | − |
| urease | − |
| hydrolysis of | |
| starch | − |
| gelatin | − |
| casein | − |
| DNA | − |
| Tween 80 | − |
| aesculin | − |
| tyrosine | |
| catabolism | − |
| use of substrate | |
| acetate | + |
| adipate | + |
| caprate | + |
| citrate | + |
| glycolate | + |
| laevulinate | + |
| malate | + |
| malonate | − |
| phenyl acetate | + |
| L-arabinose | − |
| fructose | + |
| glucose | − |
| mannose | − |
| maltose | − |
| xylose | − |
| inositol | − |
| mannitol | + |
| gluconate | + |
| N-acetylglucosamine | − |
| L-serine | − |
| L-tryptophan | + |
| acetamide | + |
| mesaconate | + |
| citraconate | + |
| L-tartrate | + |
| N-source | |
| NH$_4$+ | ++ |
| R,S-(±)-2,2-DMCPCA | + |
| butyramide | ++ |
| acetamide | + |
| propionamide | + |
| formamide | ± |
| benzamide | + |
| nicotinamide | + |

API ZONE-*Cs. acidovorans* 99.0 percent

The scientific (taxonomic) description of *Comamonas acidovorans* TG 308 (DSM No. 6552) is:

| | |
|---|---|
| cell shape | rods |
| Gram reaction (KOH test) | − |
| Gram stain | − |
| spores | − |
| mobility | + |
| °C. growth | |
| 37° C. | + |
| 41° C. | − |
| 45° C. | − |
| catalase | + |
| oxidase | + |
| fermentation in | |
| glucose (OF test) | − |
| | isolates TG308 |
| nitrate reduction | + |
| indole production | − |
| acid from glucose | − |
| arginine dehydrolase | − |
| urease | − |
| aesculin hydrolysis | − |
| gelatin hydrolysis | − |
| β-galactosidase | − |
| glucose assimilation | − |
| arabinose assimilation | − |
| mannose assimilation | − |

| -continued | |
|---|---|
| mannitol assimilation | + |
| N-acetyl-glucosamine assimilation | − |
| maltose assimilation | − |
| gluconate assimilation | + |
| caprate assimilation | + |
| adipate assimilation | + |
| malate assimilation | + |
| citrate assimilation | − |
| phenyl acetate assimilation | + |
| cytochrome oxidase | + |
| $NO_2$ from $NO_3$ | + |
| hydrolysis from urea | − |
| use of fructose | + |
| alkalization of acetamide | + |
| alkalization of tartrate | + |
| alkalization of Simmon's citrate | + |
| alkalization of malonate | (+) |
| (+) weakly positive | |

The scientific (taxonomic) description of Pseudomonas sp. NSAK: 42 (DSM No. 6433) is:

| cell shape | rods |
|---|---|
| width micron | 0.6 to 0.8 |
| length micron | 1.5 to 3.0 |
| mobility | + |
| Gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.6 | + |
| MacConkey agar | + |
| SS agar | − |
| cetrimide agar | − |
| pigments | yellow |
| acid from (OF test) | |
| glucose, aerobic | − |
| glucose, anaerobic | − |
| gas from glucose | − |
| acid from | |
| glucose | − |
| fructose | − |
| xylose | − |
| ONPG | − |
| ODC | − |
| ADH | − |
| VP | − |
| indole | − |
| $NO_2$ from $NO_3$ | − |
| denitrification | − |
| phenylalaninedesaminase | − |
| levan from saccharose | − |
| lecithinase | − |
| urease | − |
| hydrolysis of | |
| starch | − |
| gelatin | − |
| casein | − |
| DNA | − |
| Tween 80 | − |
| aesculin | − |
| tyrosine catabolism | − |
| growth material requirement | − |
| use of substrate | |
| acetate | + |
| caprate | + |
| citrate | + |
| glycolate | + |
| lactate | + |
| laevulinate | + |
| malate | + |
| malonate | + |
| phenyl acetate | + |

| -continued | |
|---|---|
| suberate | + |
| L-arabinose | − |
| fructose | + |
| glucose | − |
| mannose | − |
| maltose | − |
| xylose | − |
| mannitol | − |
| gluconate | + |
| 2-ketogluconate | + |
| N-acetylglucosamine | − |
| L-serine | + |
| L-histidine | + |
| hydroxybutyrate | + |
| N-source | |
| $NH_4^+$ | ++ |
| R,S-(±)-2,2-DMCPCA | + |

The scientific description of Bacterium sp. VIII:II (DSM No. 6316), is:

| Gram stain | + |
|---|---|
| Gram reaction (KOH test) | − |
| oxidase | − |
| catalase | − |
| nitrate reduction | − |
| tryptophan → indole | − |
| glucose (anaerobic) | − |
| arginine | − |
| urease | − |
| aesculin | + |
| gelatin | − |
| β-galactosidase | + |
| glucose | + |
| arabinose | − |
| mannose | (+) |
| mannitol | + |
| N-acetylglucosamine | − |
| maltose | + |
| gluconate | − |
| caprate | − |
| adipate | − |
| malate | − |
| citrate | − |
| phenyl acetate | − |

Initial Culture

Usually, after the selection process, an initial culture of these microorganisms is prepared, with which other cultures can then also be inoculated. The initial culture can be cultivated in the same media, with the same C/N ratio and with the same compounds as a C-source analogous to the selection process. Preferably, the medium for the initial culture contains either the composition which is indicated in Table 2 below or that which is indicated in Table 3 below with or without universal peptone. As the N-source, those usual to persons skilled in the art can be used for the initial culture, preferably an ammonium salt, such as, ammonium sulfate, is used as the N-source. The pH in the initial culture is suitably between pH 4 and 10 at a suitable temperature of 20° to 40° C. After a cultivation time of generally 10 to 100 hours, the microorganisms can be induced and prepared for the biotransformation.

Induction

Usually, the induction medium is inoculated with the initial culture, which, up to the N-source, has the same composition as the initial culture medium. For induction of the active enzymes of the microorganisms, the medium suitably contains 2,2-DMCPCA in the form of the racemate or one of its optical isomers, which can be used both as an N-source and as an enzyme inductor. But other compounds can also be used as inductors, such as, cyclopropanecarboxamide, caprolactam, benzamide, cyclohexanecarboxamide, nicotinic acid amide and crotonamide. The induction takes place suitably with 0.05 to 0.15 percent by weight, preferably with 0.1 to 0.15 percent by weight, of 2,2-DMCPCA in the form of the racemate or one of its optical isomers. After a usual induction time of 15 to 80 hours, the microorganisms can be harvested, for example, by centrifuging or ultrafiltration and then resuspended in a medium for the process.

Biotransformation

The actual process for the production of S-(+)-2,2-DMCPCA is performed according to the invention so that R-(−)-2,2-DMCPCA in racemic R,S-(±)-2,2-DMCPCA is biotransformed to R-(−)-2,2-DMCPCS, and optically active S-(+)-2,2-DMCPCA is obtained and then isolated.

Racemic R,S-(±)-2,2-DMCPCA can be produced, for example, chemically or enzymatically starting from R,S-(±)-2,2-dimethylcyclopropanecarboxylic acid nitrile.

Suitably, the biotransformation is performed either with microorganisms or with enzymes in a cell-free system.

The enzymes for the cell-free system can be obtained by breaking down the microorganism cells in a manner usual to one skilled in the art. For this purpose, for example, ultrasonic, French press or lysozyme methods can be used. The cell-free enzymes can then, for example, be immobilized for performing the process on a suitable vehicle.

Especially suitable for the process are the microorganisms of the species Comamonas acidovorans A:18 (DSM No. 6315), Comamonas acidovorans TG 308 (DSM No. 6552), Pseudomonas sp. NSAK:42 (DSM No. 6433) and the species Bacterium sp. VIII:II (DSM No. 6316), their descendants and mutants, as well as other microorganisms, which are selected according to the process described herein. The cell-free enzymes from these microorganisms are also suitable.

Preferably, the process is performed either with dormant microorganism cells (nongrowing cells), which require no more C- and N-source, or with enzymes in a cell-free system, such enzymes being obtained as described above, for example, by breaking down the induced microorganisms.

Suitably, the medium contains the racemic 2,2-DMCPCA in an amount of 0.2 to 5 percent by weight, preferably 0.2 to 2 percent by weight. As a medium for the process, those usual to persons skilled in the art can be used, such as, low-molecular phosphate buffers, the above-described mineral salt medium or else HEPES buffer (N-2-hydroxyethylpiperazine-2'-ethanesulfonic acid). Preferably, the process is performed in a low-molecular phosphate buffer. The pH of the medium can be in a range of pH 6 to 11; preferably the pH is between 6.5 and 10. Suitably, the biotransformation is performed at a temperature of 15° to 55° C., preferably at 20° to 40° C. After a usual reaction time of 1 to 30 hours, preferably 5 to 25 hours, R-(−)-2,2-DMCPCA is completely converted to the corresponding acid, and optically pure S-(+)-2,2-DMCPCA is obtained. The thus-obtained S-(+)-2,2-DMCPCA can then be obtained, for example, by extraction, electrodialysis or drying.

EXAMPLE 1

Isolation and Selection of Microorganisms with a R-(−)-2,2-DMCPCA-Hydrolase

Isotonic common salt solution (9 ml) was added to crushed samples of earth (1 g) and all of this was allowed to stand for about 5 minutes. Then, the supernatant (0.5 ml) was inoculated in a mineral salt medium (25 ml) [Kulla et al., Arch. Microbiol. 135, (1983), pages 1 to 7], which contained glycerin and R,S-(±)-DMCPCA in a C/N ratio of 5:1. Then, the culture was incubated until a mixed culture resulted, which can use R,S-(±)-2,2-DMCPCA as an N-source. Pure cultures of these microorganisms were obtained with the aid of traditional microbiological techniques. The microorganism strains obtained in this way were then tested on agar plates for their growth to R,S-(±)-2,2-DMCPCA, S-(+)-2,2-DMCPCA and R-(−)-2,2-DMCPCA to find the undesired strains, which grow equally quickly on both isomers [R-(−)-2,2-DMCPCA and S-(+)-2,2-DMCPCA]. The usual strains were further tested. With the latter, an initial culture medium was then inoculated. The microorganisms obtained in this initial culture were converted into the mineral salt medium and then examined for their ability selectively to use R-(−)-2,2-DMCPCA as the sole N-source, and the supernatant was examined by GC for the formation of R-(−)-2,2-DMCPCS and for the concentration of S-(+)-2,2-DMCPCA.

EXAMPLE 2

Determination of Activity of R-(−)-2,2-DMCPCA-Hydrolase

To determine the activity of the hydrolase, the microorganism suspension was adjusted to an optical density of 0.5 at 650 nm. As a medium, a phosphate buffer (10 mmol), pH 7.0, with 0.2 percent by weight of R,S-2,2-DMCPCA, was used. This suspension was incubated for 3 hours at 30° C. with shaking. The $NH_4^+$ released by the hydrolase or the R-(−)-2,2-DMCPCS was measured and the activity reacted as g of R-(−)-2,2-DMCPCA was expressed /l/h/ optical density at 650 nm, provided that 1 mmol of formed $NH_4^+$ equals 1 mmol of reacted R-(−)-2,2-DMCPCA.

TABLE 1

Determination of the hydrolase activity as a function of the temperature (strain Comamonas acidovorans A:18, DSM No. 6315)

| Temperature [°C.] | Activity g/l/h/$OD_{650}$ |
|---|---|
| 25 | 0.25 |
| 30 | 0.5 |
| 37 | 1.0 |
| 45 | 1.5 |
| 48 | 1.8 |
| 55 | 1.9 |
| 65 | 0 |

EXAMPLE 3

Production of S-(+)-2,2-DMCPCA

Comamonas acidovorans A:18 was incubated on mineral salt medium-agar plates with glycerin as a C-source and ammonium sulfate as an N-source for 2 days at 30° C. The composition of the mineral salt medium is indicated in Table 2 below. With these plated-out microorganisms, an initial culture medium with the same composition was inoculated and incubated for 2 days at 30°

C. The same mineral salt medium with Na$_2$SO$_4$ instead of (NH$_4$)$_2$SO$_4$ (100 ml) containing 0.2 percent by weight of glycerin and 0.15 percent by weight of R,S-($\pm$)-2,2-DMCPCA was inoculated with 5 ml of this initial culture for induction and incubated at 30° C. for 45 hours. Then, the cells were harvested by centrifuging and taken up in 0.9 percent NaCl solution. After resuspension of the cells in 10 mmol of phosphate buffer (800 ml), pH 7.0, an optical density of 1.3 was adjusted at 650 nm and 2 percent by weight of R,S-($\pm$)-2,2-DMCPCA was added. After an incubation of about 25 hours at 37° C., R-(−)-2,2-DMCPCA was completely reacted to R-(−)-2,2-DMCPCS, which corresponded to an optical purity (ee) of 100 percent and an analytically measured yield in S-(+)-2,2-DMCPCA of 46.7 percent. The course of the reaction was tracked based on the release of NH$_4^+$ and based on the GC analysis of the supernatant. After the centrifuging off of the cells, the supernatant was adjusted to a pH of 9.5 and the product was isolated by extraction with ethyl acetate.

EXAMPLE 4

Analogously to Example 1, microorganism Bacterium sp. VIII:II, was isolated. The initial cultivating time was 4 days in the case of this microorganism and the induction time was 3 days under the otherwise same conditions as Example 3.

In contrast to Example 3, the biotransformation in this microorganism was performed with 0.2 percent by weight of R,S-($\pm$)-2,2-DMCPCA, and the activity of the hydrolase was determined as 0.13 g/1/h/OD$_{650nm}$.

TABLE 2

Medium-composition of the initial culture
[Kulla et al., Arch. Microbiol. 135, (1983), pages 1 to 7]

| g/l of distilled water pH 7.0 | |
|---|---|
| 2.0 | (NH$_4$)$_2$SO$_4$ |
| 2.5 | Na$_2$HPO$_4$.2H$_2$O |
| 1.0 | KH$_2$PO$_4$ |
| 3.0 | NaCl |
| 0.4 | MgCl$_2$.6H$_2$O |
| 0.015 | CaCl$_2$.2H$_2$O |
| 0.0008 | FeCl$_2$.6H$_2$O |
| 0.0001 | ZnSO$_4$.7H$_2$O |
| 0.00009 | MnCl$_2$.4H$_2$O |
| 0.0003 | H$_3$BO$_3$ |
| 0.0002 | CoCl$_2$.6H$_2$O |
| 0.00001 | CuCl$_2$.2H$_2$O |
| 0.00002 | NiCl$_2$.6H$_2$O |
| 0.00003 | Na$_2$MoO$_4$.2H$_2$O |
| 0.005 | Na$_2$ EDTA.2H$_2$O |
| 0.002 | FeSO$_4$.7H$_2$O |
| 2 | Glycerin |

EXAMPLE 5

Analogously to Example 1, Pseudomonas sp. NSAK:42 (DSM No. 6433) was isolated. The initial cultivation time was 2 days, and the induction time was 18 hours, under the otherwise same conditions as Example 3, with the exception that the induction medium contained 1 percent by weight of glycerin (instead of 0.2 percent by weight) and in addition another 0.3 percent by weight of universal peptone (Merck). The biotransformation was performed with 0.2 percent by weight of R,S-($\pm$)-2,2-DMCPCA, and the activity of the hydrolase was determined as 0.34 g/1/h/OD$_{650nm}$.

EXAMPLE 6

Comamonas acidovorans TG 308 (DSM No. 6552), was cultivated for 2 days at 30° C. in the complex medium (4 ml) "nutrient broth" (Oxoid Ltd., GB). With these microorganisms, a mineral salt medium (Table 3) was inoculated and incubated for 2 days at 30° C. Then, the cells were harvested according to Example 3. In contrast to Example 3, the biotransformation in 10 mmol of HEPES buffer (pH 7.0) was performed with 0.5 percent by weight of R,S-($\pm$)-2,2-DMCPCA under the otherwise same conditions as in Example 3. After an incubation of 4.5 hours at 37° C., R-(−)-2,2-DMCPCA was completely reacted to R-(−)-2,2-DMCPCS, which corresponded to an analytically measured yield of S-(+)-DMCPCA of 45.5 percent and an optical purity (ee) of 99.0 percent.

TABLE 3

| g/l of distilled water pH 7.0 | |
|---|---|
| 2.0 | K$_2$HPO$_4$ |
| 2.0 | KH$_2$PO$_4$ |
| 2.0 | MgSO$_4$.7H$_2$O |
| 0.5 | yeast extract |
| 2.0 | universal peptone (Merck) |
| 2.0 | NaCl |
| 0.01 | FeCl$_2$.H$_2$O |
| 10 | sodium glutamate |
| 5 | crotonamide |

EXAMPLE 7

Production of S-(+)-2,2-DMCPCA with Enzymes in a Cell-Free System

After induction, the cells of Comamonas acidovorans A:18 were concentrated to an optical density at 650 nm from 210 to 95 ml in the HEPES buffer (10 mM, pH 7.0). Then, the cells were broken down twice in the French press at a pressure of 1200 bars. To obtain a cell-free enzyme extract, all of this material was then centrifuged at 20,000 rpm for 20 minutes. In this cell-free enzyme extract, the amount of protein (measured according to the Bradford method) was then determined as 39.3 mg of protein/ml. To determine the activity of these cell-free enzymes, 20 microliters (about 0.8 mg of protein) of this cell-free enzyme extract was taken up in 4 ml of phosphate buffer (10 mM, pH 7.0), containing 0.2 percent by weight of R,S-($\pm$)-2,2-DMCPCA and incubated at 30° C. Here, 2.5 g of R-(−)-2,2-DMCPCA/h/g of protein (3.64 micromol/min/g of protein) was converted to the corresponding acid.

EXAMPLE 8

Production of S-(+)-2,2-DMCPCA with Immobilized Cells

After induction (corresponding to Example 3), the cells of Comamonas acidovorans A:18, were harvested. These cells were immobilized by a polyethylene imine/-glutaraldehyde treatment (corresponding to Czechoslovakian Patent No. 251,111). The immobilized biocatalyst had an activity of 1.6 micromol/min g of dry weight. The dry weight of the biocatalyst corresponded to 32 percent of the moist weight. Then, the biocatalyst (with 55 g moist weight) was suspended in 800 ml of boric acid (10 mM, pH 9.0) with 16 g of R,S-($\pm$)-2,2-DMCPCA. After an incubation time of 68.8 hours at 37 C and at a stirring speed of 200 rpm, R-(−)-2,2-DMCPCA was completely reacted to R-(−)-2,2-DMCPCS, which corresponded to an optical purity (ee) of 98.2 percent and an analytically measured yield in S-(+)-2,2-DMCPCA of 40 percent.

What is claimed is:

1. A process for the production of S-(+)-2,2-dimethylcyclopropanecarboxamide, comprising biotransforming R-(−)-2,2-dimethylcyclopropanecarboxamide in racemic R,S-(±)-2,2-dimethylcyclopropanecarboxamide with a microorganism or with an enzyme from the microorganism in a cell-free system to R-(−)-2,2-dimethylcyclopropanecarboxylic acid, the microorganism being Comamonas acidovorans A:18 (DSM No. 6315) or a mutant thereof which retains the capacity to perform the biotransformation, or Comamonas acidovorans TG 308 (DSM No. 6552) or a mutant thereof which retains the capacity to perform the biotransformation, or Pseudomonas sp. NSAK:42 (DSM No. 6433) or a mutant thereof which retains the capacity to perform the biotransformation, or Bacterium sp. VIII:II (DSM No. 6316) or a mutant thereof which retains the capacity to perform the biotransformation, and obtaining optically active S-(+)-2,2-dimethylcyclopropanecarboxamide and isolating the latter compound.

2. The process according to claim 1 wherein the biotransformation is performed with cell-free enzymes from Comamonas acidovorans A:18 (DSM No. 6315), or a mutant thereof which retains the capacity to perform the biotransformation.

3. The process according to claim 1 wherein the biotransformation is performed with cell-free enzymes from Comamonas acidovorans TG 308 (DSM No. 6552), or a mutant thereof which retains the capacity to perform the biotransformation.

4. The process according to claim 1 wherein the biotransformation is performed with cell-free enzymes from Pseudomonas sp. NSAK:42 (DSM No. 6433), or a mutant thereof which retains the capacity to perform the biotransformation.

5. The process according to claim 1 wherein the biotransformation is performed with cell-free enzymes from Bacterium sp. VIII:II (DSM No. 6316), or a mutant thereof which retains the capacity to perform the biotransformation.

6. The process according to claim 1 wherein the biotransformation is performed with Comamonas acidovorans A:18 (DSM No. 6315), or a mutant thereof which retains the capacity to perform the biotransformation.

7. The process according to claim 1 wherein the biotransformation is performed with Comamonas acidovorans TG 308 (DSM No. 6552), or a mutant thereof which retains the capacity to perform the biotransformation.

8. The process according to claim 1 wherein the biotransformation is performed with Pseudomonas sp. NSAK:42 (DSM No. 6433), or a mutant thereof which retains the capacity to perform the biotransformation.

9. The process according to claim 1 wherein the biotransformation is performed with Bacterium sp. VIII:II (DSM No. 6316), or a mutant thereof which retains the capacity to perform the biotransformation.

10. The process according to claim 1 wherein the biotransformation is performed in a medium containing racemic 2,2-dimethylcyclopropanecarboxamide in an amount of 0.2 to 5 percent by weight.

11. The process according to claim 10 wherein the biotransformation is performed at a pH of 6 to 11 and at a temperature of 15° to 55° C.

12. The process according to claim 11 wherein the biotransformation is performed with Comamonas acidovorans A:18 (DSM No. 6315), or a mutant thereof which retains the capacity to perform the biotransformation.

13. The process according to claim 11 wherein the biotransformation is performed with Comamonas acidovorans TG 308 (DSM No. 6552), or a mutant thereof which retains the capacity to perform the biotransformation.

14. The process according to claim 11 wherein the biotransformation is performed with Pseudomonas sp. NSAK:42 (DSM No. 6433), or a mutant thereof which retains the capacity to perform the biotransformation.

15. The process according to claim 11 wherein the biotransformation is performed with Bacterium sp. VIII:II (DSM No. 6316), or a mutant thereof which retains the capacity to perform the biotransformation.

16. The process according to claim 1 wherein the biotransformation is performed with an enzyme from a microorganism in a cell-free system.

17. The process according to claim 16 wherein the biotransformation is performed in a medium containing racemic 2,2-dimethylcyclopropanecarboxamide in an amount of 0.2 to 5 percent by weight.

18. The process according to claim 17 wherein the biotransformation is performed at a pH of 6 to 11 and at a temperature of 15° to 55° C.

19. The process according to claim 18 wherein the biotransformation is performed with cell-free enzymes from Comamonas acidovorans A:18 (DSM No. 6315), or a mutant thereof which retains the capacity to perform the biotransformation.

20. The process according to claim 18 wherein the biotransformation is performed with cell-free enzymes from Comamonas acidovorans TG 308 (DSM No. 6552), or a mutant thereof which retains the capacity to perform the biotransformation.

21. The process according to claim 18 wherein the biotransformation is performed with cell-free enzymes from Pseudomonas sp. NSAK:42 (DSM No. 6433), or a mutant thereof which retains the capacity to perform the biotransformation.

22. The process according to claim 18 wherein the biotransformation is performed with cell-free enzymes form Bacterium sp. VIII:II (DSM No. 6316), or a mutant thereof which retains the capacity to perform the biotransformation.

* * * * *